United States Patent
Cohen et al.

(10) Patent No.: US 7,666,144 B2
(45) Date of Patent: Feb. 23, 2010

(54) METHODS AND APPARATUS FOR DETERMINING CARDIAC OUTPUT AND LEFT ATRIAL PRESSURE

(75) Inventors: Richard J. Cohen, Chestnut Hill, MA (US); Ramakrishna Mukkamala, Lansing, MI (US)

(73) Assignees: Board of Trustees Operating Michigan State University, East Lansing, MI (US); Massachusetts Institute of Technology, Cambridge, MA (US)

( * ) Notice: Subject to any disclaimer, the term of this patent is extended or adjusted under 35 U.S.C. 154(b) by 250 days.

(21) Appl. No.: 11/358,379

(22) Filed: Feb. 21, 2006

(65) Prior Publication Data

US 2007/0197921 A1 Aug. 23, 2007

(51) Int. Cl.
A61B 5/02 (2006.01)

(52) U.S. Cl. .................................................. 600/485
(58) Field of Classification Search .................. 600/485
See application file for complete search history.

(56) References Cited

U.S. PATENT DOCUMENTS 6,506,163 B1 * 1/2003 Farrell et al. ............... 600/486

7,398,688 B2 * 7/2008 Zdeblick et al. ............ 73/700

* cited by examiner

Primary Examiner—Charles A Marmor, II
Assistant Examiner—Christian Y Jang
(74) Attorney, Agent, or Firm—Harness, Dickey & Pierce, P.L.C.

(57) ABSTRACT

Method and apparatus are introduced for determining proportional cardiac output (CO), absolute left atrial pressure (LAP), and/or other important hemodynamic variables from a contour of a circulatory pressure waveform or related signal. Certain embodiments of the invention provided herein include the mathematical analysis of a pulmonary artery pressure (PAP) waveform or a right ventricular pressure (RVP) waveform in order to determine beat-to-beat or time-averaged proportional CO, proportional pulmonary vascular resistance (PVR), and/or LAP. The invention permits continuous and automatic monitoring of critical hemodynamic variables with a level of invasiveness suitable for routine clinical application. The invention may be utilized, for example, to continuously monitor critically ill patients with pulmonary artery catheters installed and chronically monitor heart failure patients instrumented with implanted devices for measuring RVP.

20 Claims, 6 Drawing Sheets

METHODS AND APPARATUS FOR DETERMINING CARDIAC OUTPUT AND LEFT ATRIAL PRESSURE

BACKGROUND OF THE INVENTION

Cardiac output (CO) is the volume of blood ejected by the heart per unit time, while left atrial pressure (LAP) generally indicates the blood pressure attained in the left ventricle during the filling phase of the cardiac cycle. CO and LAP are perhaps the two most important quantities to be able to monitor in critically ill patients, as they facilitate the diagnosis, monitoring, and treatment of various disease processes such as left ventricular failure, mitral valve disease, and shock of any cause [36]. For example, a decrease in CO while LAP is rising would indicate that the patient is in left ventricular failure, whereas a decrease in CO while LAP is falling would indicate that the patient might be going into hypovolemic shock.

Several methods are currently available for monitoring CO or LAP. While each of these methods can offer some advantages, as described below, all of the methods are limited in at least one clinically significant way.

The standard methods intended for monitoring CO and LAP in critically ill patients both involve the use of the balloon-tipped, flow-directed pulmonary artery catheter [47,70]. This catheter also permits continuous monitoring of pulmonary artery pressure (PAP) and central venous pressure (i.e., right ventricular filling pressure) via fluid-filled systems attached to external pressure transducers. (However, the most common reason for inserting the pulmonary artery catheter is perhaps in an effort to monitor LAP [46].) CO is specifically estimated according to the thermodilution method [17,47]. This method involves injecting a bolus of cold saline in the right atrium, measuring temperature downstream in the pulmonary artery, and computing the average CO based on conservation laws. LAP is estimated through pulmonary capillary wedge pressure (PCWP), which is determined by advancing the catheter into a branch of the pulmonary artery, inflating the balloon, and averaging the ensuing steady-state pressure [47].

Since PCWP is measured when flow has ceased through the branch, in theory, the PCWP should provide an estimate of LAP. However, the PCWP is not equal to LAP and is only an approximation [31,44]. In fact, as a result of a number of technical problems, in practice, the PCWP method frequently provides only a poor estimate of LAP. These problems include partial wedging and balloon over-inflation [38,53], dependence of the measurement on the wedge catheter position [27,33], and inter-clinician variability in interpreting the phasic PCWP measurement [37]. Indeed, the developers of the PCWP method and the balloon-tipped, flow-directed catheter each reported that they could satisfactorily measure PCWP only about three quarters of the time [58,70]. In 2,711 PCWP measurement attempts made in the ICU, Morris et al reported that only 69% of these attempts were successful with only 10% of the unsatisfactory measurements due to easily correctable damped tracings [53]. Similar technical problems are also encountered in implementing the thermodilution method in which variations in injectate volume, rate, and temperature introduce error in the measurement, which is known to be in the 15-20% range [39,50,68]. Also, the very injection of fluid and balloon inflation poses some risk to the patient [17,34,42]. Perhaps, as a result of these shortcomings, the clinical benefit of the pulmonary artery catheter has yet to be clearly established (e.g., [64]). In addition, a major limitation of the thermodilution and PCWP methods is that an operator is required. Thus, these important measurements are only made every few hours.

Alternative methods for monitoring CO include the aortic flow probe, oxygen Fick, dye-dilution, continuous thermodilution, Doppler ultrasound, and thoracic bioimpedance. The aortic flow probe uses ultrasound transit-time (or electromagnetic) principles to measure instantaneous flow [17]. While this method is continuous and very accurate, it requires the placement of the flow probe directly around the aorta and is therefore much too invasive for most clinical applications. The oxygen Fick method involves simultaneous measurement of central venous and arterial oxygen content of blood and measurement of ventilatory oxygen uptake [17]. Although this method is also highly regarded in terms of its accuracy, it is too cumbersome for frequent clinical application. The dye dilution method involves the injection of a dye into the right atrium and serial measurement of the dye concentration in blood samples drawn from an arterial catheter [17]. The related thermodilution method is generally preferred over this method, because thermodilution requires only one catheter and is less affected by indicator recirculation. The continuous thermodilution method involves automatic heating of blood in the right atrium via a thermal filament, measurement of the temperature changes downstream in the pulmonary artery, and computation of average flow via cross correlation and bolus thermodilution principles [17,76]. While this method does not require an operator, the temperature changes generated by the thermal filament must be small to avoid damaging tissue and blood [17]. As a result, the signal to noise ratio of continuous thermodilution is small compared to standard thermodilution, which may render the continuous approach to be less accurate [78]. Doppler ultrasound methods generally measure the Doppler shift in the frequency of an ultrasound beam reflected from the flowing aortic blood [17]. These non-invasive methods are not commonly employed in critical care medicine, because they require expensive capital equipment and an expert operator to stabilize an external ultrasound transducer [40]. Thoracic bioimpedance involves measuring changes in the electrical impedance of the thorax during the cardiac cycle [17,40]. Although this method is non-invasive and continuous, it is too inaccurate for use in critically ill patients due to excessive lung fluids [11].

Alternative methods for monitoring LAP include direct left heart catheterization, physical examination, and Doppler imaging. Direct catheterization of the left heart is the gold standard method permitting continuous and accurate monitoring of LAP [65]. However, this method is too invasive and risky for routine clinical application. In a physical examination, clinical and radiographic signs of congestion such as rales, third heart sound, prominent jugular vein, and interstitial and alveolar edema are utilized to obtain a qualitative indication of elevated LAP in patients typically with heart failure [9]. While this approach is simple and non-invasive, it is neither continuous nor has it been shown to be sensitive to at least changes in PCWP [9,16,69]. In Doppler imaging methods (e.g., color M-mode Doppler, tissue Doppler, pulsed Doppler), parameters such as transmitral and pulmonary venous velocity profiles are obtained to qualitatively monitor LAP changes or quantitatively monitor PCWP through empirical formulas [21,22,57]. Although these techniques may also be non-invasive, they are expensive, can only be used intermittently, and are not specific and may therefore be inaccurate [2,57, 62].

It would be desirable to be able to accurately monitor both CO and LAP by analysis of a PAP waveform, a right ventricular pressure (RVP) waveform, or other circulatory signals. Thus, unlike the aforementioned methods, this approach would permit continuous and automatic measurement of these two critically important hemodynamic variables with a level of invasiveness suitable for routine clinical use. A continuous and automatic monitoring approach would be desirable for several reasons. Continuous monitoring of both CO and LAP would be a great advantage during fluid and pharmaceutical interventions, as the clinician would be able to assess the effects of the interventions and be quickly alerted to possible complications. Continuous monitoring would also provide an early indication of deleterious hemodynamic events induced by disease (e.g., hypovolemia via simultaneously decreasing CO and LAP). Moreover, automatic monitoring would save precious time in the busy intensive care unit (ICU) and operating room (OR) environments [17] and circumvent the clinically significant problems associated with implementing the standard measurement methods (see above). Finally, the approach would be a tremendous advantage in the context of remote ICU monitoring (e.g., [63]) and ambulatory monitoring of PAP or RVP waveforms (in, for example, heart failure patients) via available implanted devices [1,67]. A method for such chronic monitoring of both of these two valuable hemodynamic variables does not otherwise exist.

Many investigators have sought analysis techniques to continuously monitor CO from arterial pressure waveforms. Such techniques have been proposed for over a century [19].

Much of the earlier work assumed that either arterial tree is well represented by a Windkessel model accounting for the compliance of the large arteries and the vascular resistance of the small arteries. FIG. 1 illustrates the electrical analog of a Windkessel model of the systemic arterial tree. (Because systemic vascular resistance (SVR) is relatively large, the model here assumes that the systemic venous pressure (SVP) is negligible with respect to the systemic arterial pressure (SAP) by virtue of SVR being referenced to atmospheric pressure rather than SVP.) While techniques based on this simple model generally failed when applied to SAP waveforms measured centrally in the aorta (e.g., [66,72]), Bourgeois et al showed that their technique yielded a quantity that varied linearly with aortic flow probe CO over a wide physiologic range [6]. The key concept of their technique is that, according to the Windkessel model, SAP should decay like a pure exponential during each diastolic interval with a time constant ($\tau$) equal to the product of SVR and systemic arterial compliance (AC). Since AC is nearly constant over a wide pressure range and on the time scale of months [5,26,60], CO could then be measured to within a constant scale factor by dividing the time-averaged SAP with $\tau$. Thus, the technique of Bourgeois et al involves fitting an exponential function to each diastolic interval of a SAP waveform to measure $\tau$ (FIG. 1).

Bourgeois et al were able to validate their technique with respect to central SAP waveforms, because the diastolic interval of these waveforms can sometimes resemble an exponential decay following incisura (FIG. 2a). These investigators identified a precise location in the thoracic aorta as the optimal site in the canine for observing an exponential diastolic decay. However, central SAP is rarely measured clinically due to the risk of blood clot formation and embolization. Moreover, exponential diastolic decays are usually not apparent in either peripheral SAP waveforms (FIG. 2b), which may be measured via minimally invasive radial artery catheterization, or PAP waveforms (FIG. 2c). Indeed, Bourgeois et al acknowledged that exponential diastolic decays are obscured in peripheral SAP waveforms [5]. Moreover, after Engelberg et al suggested that the pulmonary arterial tree be represented by a Windkessel model in which the small pulmonary vascular resistance (PVR) is referenced to LAP (electrical analog in FIG. 3) [18], Milnor et al attempted to fit an exponential function to each diastolic decay interval of PAP waveforms minus average LAP in man and reported that all of the waveforms were not adequate for doing so [51]. Subsequently, Tajimi et al reported that they were not able to identify a location in the canine or human pulmonary artery in which exponential diastolic pressure decays were consistently visible [71]. The reason is that the systemic and pulmonary arterial trees are not simply lumped systems like the Windkessel model suggests but rather complicated distributed systems with impedance mismatches throughout due to vessel tapering, bifurcations, and caliber changes. The diastolic (and systolic) intervals of peripheral SAP and PAP waveforms are therefore corrupted by complex wave reflections occurring at each and every site of impedance mismatch. Moreover, inertial effects also contribute to obscuring exponential diastolic decays, especially in the low-pressure pulmonary arterial tree [55]. Thus, the technique of Bourgeois et al cannot be applied to clinically measurable peripheral SAP and PAP waveforms.

More recently, investigators have attempted to monitor CO from peripheral SAP waveforms. Techniques based on an adaptive aorta model, which require SAP waveforms measured at both the carotid and femoral arteries have been proposed [59,73]. However, catheters are usually not placed for prolonged periods of time at either of these sites in ICUs, ORs, or recovery rooms due to safety considerations. A technique has been introduced that is based on an empirically derived formula involving the calculation of the derivative of the ABP waveform [23]. However, in order to mitigate the corruptive effects of wave reflections on the derivative calculation, this technique also requires two peripheral ABP measurements, one of which is obtained from the femoral artery. Learning techniques requiring training data sets consisting of simultaneous measurements of CO and SAP waveforms have also been suggested [8,24,48]. However, these techniques were only demonstrated to be successful in central ABP waveforms or over a narrow physiologic range. Moreover, learning techniques could only be successful provided that the available training set of patient data reflected the entire patient population. Finally, Wesseling et al [3,74] and Linton et al [41] have proposed techniques requiring only the analysis of a single radial SAP waveform. However, Linton et al only showed that their technique was accurate over a narrow physiologic range, and several studies have demonstrated limitations of the technique of Wesseling et al (e.g., [20,29]).

A technique for continuous CO monitoring from peripheral SAP waveforms has been the recent focus of interest, because it is minimally invasive or possibly even non-invasive (e.g., [24]). However, even if such a technique were introduced with sufficient accuracy, the more invasive pulmonary artery catheters would still be used to be able to measure left and right ventricular filling pressures. Four investigators have therefore previously attempted to monitor CO continuously by analysis of PAP waveforms [10,15,71,77]. In this way, ventricular filling pressures and continuous CO could be measured with a single catheter. These investigators essentially employed analysis techniques that were previously applied to SAP waveforms. Their results showed that the techniques could estimate CO during cardiac interventions but not vascular interventions (e.g., volume infusion). Moreover, even though LAP is also a significant determinant of PAP and should therefore be reflected in the PAP waveform, none of these techniques included a means to monitor LAP. In fact, similar to the suggestion of Engelberg et al, the technique of Cibulski et al actually required an additional LAP measurement for monitoring CO [10].

The common feature of all of the aforementioned techniques for monitoring CO from continuous SAP or PAP is that the waveform analysis is employed only over time scales within a cardiac cycle. Because of the corruptive effects of highly complex waves at these time scales, the techniques were limited in that they 1) could only be applied to highly invasive central SAP waveforms in which the complex wave reflections may be attenuated; 2) necessitated multiple peripheral SAP waveform measurements (which are rarely obtained clinically); 3) required an exhaustive training data set, and/or 4) are accurate only over a narrow physiologic range or only during cardiac interventions. However, the confounding effects of wave as well as inertial phenomenon are known to diminish with increasing time scale [55]. Based on this under-appreciated concept, Mukkamala et al introduced a technique to monitor CO by analyzing a single arterial pressure waveform (measured at any site in the systemic or pulmonary arterial trees) over time scales greater than a cardiac cycle [54]. They evaluated their technique with respect to peripheral SAP waveforms in swine and their results showed excellent agreement with aortic flow probe measurements over a wide physiologic range [54]. While this technique may permit continuous and accurate monitoring of CO with a level of invasiveness suitable for routine clinical application, it does not provide a convenient means to monitor LAP.

Some investigators have attempted to monitor LAP or PCWP by analysis of blood pressure waveforms. Shortly after the introduction of the pulmonary artery catheter, researchers studied the end-diastolic PAP as a continuous index of LAP [28,31]. However, this simple technique is not as accurate as the PCWP method [31] (see below) and becomes unreliable when the rate of drainage of blood from the pulmonary artery into the pulmonary capillaries is slow. Thus, for example, it is well known that the end-diastolic PAP is not an acceptable index of LAP in patients with pulmonary vascular disease [28]. More recently, a learning technique has been proposed to monitor PCWP from a PAP waveform using an artificial neural network trained on a database of PCWP measurements and PAP waveforms [14, 78]. However, this technique was shown to be ineffective when the network was trained on one set of subjects and tested on a different set of subjects [14]. Finally, techniques have been proposed in which trained regression equations predict LAP or PCWP from variations in parameters of the SAP or plethysmographic waveform (e.g., systolic pressure, pulse pressure) in response to the Valsalva maneuver or mechanical positive pressure ventilation [45,49,65,75]. While these techniques may be minimally invasive or non-invasive, they are either not continuous or applicable to subjects breathing spontaneously. Moreover, since SAP and related signals are also due to ventricular and arterial functionality, these techniques do not provide a specific measure of LAP or PCWP and may therefore be inaccurate [13].

Thus, a technique is needed that accurately monitors both CO and LAP by analysis of a PAP waveform, a RVP waveform, or other circulatory signals. Such a technique could be utilized, for example, to continuously monitor critically ill patients instrumented with pulmonary artery catheters and chronically monitor heart failure patients instrumented with implanted devices.

SUMMARY OF THE INVENTION

The present invention involves the mathematical analysis of the contour of a PAP waveform, a RVP waveform, or another circulatory signal in order to determine average LAP, average SVP, proportional CO, proportional PVR, proportional SVR, and/or other clinically important hemodynamic variables. In various embodiments, the methods of the invention may be employed to make individual measurements of average LAP, average SVP, proportional CO, proportional PVR, proportional SVR, and/or other clinically important hemodynamic variables at one or more time instances or may be employed for continuous monitoring of one or more of these variables.

The mathematical analysis of a circulatory contour is defined here to comprise an examination of the temporal variations in the signal. The temporal variations in the signal can be examined within a single cardiac cycle, between different cardiac cycles, or both. Simply monitoring the signal at the same time instance relative to a physiologically significant event, such as the end of diastole or the end of systole, in multiple cycles does not constitute performing a mathematical analysis of a circulatory contour. Furthermore, the above definition is intended to exclude trivial examinations of the temporal variations in the signal that solely provide an estimate of the time instance of such a physiologically significant event (e.g., zero temporal derivative of the signal). Thus, for example, monitoring LAP via the end-diastolic PAP does not constitute a mathematical analysis of a circulatory contour even if the time instance of the end of diastole is determined via the zero temporal derivative of the PAP waveform (i.e., the time point at which the derivative of the PAP waveform is zero), since in effect this examination indicates PAP at particular instances of time.

Typically, an examination of the temporal variations in the signal involves the analysis of at least two time instances of the signal within a single cardiac cycle or at least two time instances of the signal within at least two cardiac cycles. In certain embodiments of the invention, an examination of the temporal variations in the signal involves the analysis of an interval of the signal within a cardiac cycle (e.g., fraction of the diastolic interval greater than 25%) or encompassing multiple cardiac cycles (e.g., at least 30 cardiac cycles). In certain embodiments of the invention, an examination of the temporal variations in the signal involves the analysis of an interval of the signal within individual cardiac cycles (e.g., systolic ejection interval) over a period encompassing multiple cardiac cycles (e.g., at least 30 cardiac cycles). In various embodiments of the invention the average values for hemodynamic variables computed as described herein may be averages over a single beat or over multiple beats.

In certain embodiments of the invention, the mathematical analysis of a circulatory contour involves the use of the Windkessel model of FIG. 3 to represent the slow dynamical properties of the pulmonary arterial tree.

In one such embodiment, proportional CO, average LAP, and other hemodynamic variables such as proportional PVR are determined by mathematical analysis of one or more individual diastolic decay interval(s) of a PAP waveform. For example, in certain embodiments of the invention, a set of basis functions, one or more of which may include a constant term or may be a constant term, are fitted to each diastolic decay interval of PAP to respectively determine the dynamical properties of the pulmonary arterial tree and the average LAP. Any basis functions known in the art may be employed. For example, real exponentials, complex exponentials, and/or polynomials (e.g., over a specific time interval) can be used.

In certain embodiments of the invention, complex exponential functions and a constant term are fitted to each diastolic decay interval of PAP to respectively determine the dynamical properties of the pulmonary arterial tree and the average LAP (FIG. 4). Any number of complex exponential functions (usually an odd number) may be utilized in the fitting procedure to account for wave, inertial, and Windkessel effects in the pulmonary arterial tree. The fitting procedure may be performed using any method known in the art and applied to, for example, the entire PAP downstroke (i.e., from maximum to minimum pressure; FIG. 4). Then, the Windkessel time constant τ is determined by, for example, extrapolating the computed exponential functions to low-pressure values and fitting a mono-exponential function to the extrapolated pressure values for which the faster wave and inertial effects have dissipated or vanished (FIG. 4). The average LAP is determined by, for example, computing the mean value of the resulting constant term (i.e., the constant term that the mono-exponential function approaches asymptotically) over any number of beats, while proportional CO is determined, for example, by computing the mean value of the resulting PAP-LAP (i.e., the mean value resulting from subtracting the LAP from PAP) over any number of beats and dividing this quantity by the mean value of the corresponding τ.

In other embodiments of the invention, the set of basis functions is a set of decaying polynomial functions, at least one of which is or includes a constant term. The polynomials may be extrapolated to low pressure values, and a single exponential can then be fitted to the low pressure values to determine the time constant. Alternatively, the basis functions can be extrapolated to low pressure values, and the time constant may be measured from the extrapolated pressure values by any other method known in the art (e.g., the time duration required for the extrapolated pressure to drop by a predetermined amount, such as by a factor of $e^{-1}$ (36.79%). It will be appreciated that other methods for determining average LAP from the unknown constant, e.g., without performing extrapolation, may also be used.

In another such embodiment, proportional CO, average LAP, and/or other hemodynamic variables such as proportional PVR are determined by mathematical analysis of all temporal variations in a PAP waveform including those occurring over time scales greater than a cardiac cycle in which the confounding effects of wave and inertial phenomena are attenuated [55]. For example, a segment of a PAP waveform of duration greater than a cardiac cycle (e.g., ranging from 30 seconds to ten-minutes) is fitted according to the sum of an unknown constant term representing average LAP and the convolution of an unknown impulse response characterizing the dynamical properties of the pulmonary arterial tree with a known signal reflecting each cardiac contraction. The cardiac contractions signal may be established from the PAP waveform and possibly other physiologic signals by, for example, forming an impulse train in which each impulse is located at the onset of each cardiac contraction and has area equal to an arbitrary constant, the ensuing pulse pressure (x(t) in FIG. 5), or any other value based on the PAP pulse (e.g., the ensuing pulse pressure determined after lowpass filtering the PAP waveform to attenuate the wave and inertial effects or the value of PAP at any defined time instance in the cardiac cycle relative to the onset of a cardiac contraction with or without respect to the value of PAP at the cardiac contraction onset). The unknown constant term and impulse response are determined so as to permit the best fit of the PAP waveform segment according to any of the methods known in the art. The process of determining the unknown constant term and impulse response that provide the best fit, or an acceptable fit, to a waveform or portion thereof is referred to as "fitting" herein. The resulting pulmonary arterial tree impulse response is defined to represent the PAP-LAP response to a single, solitary cardiac contraction (h(t) in FIG. 5). The Windkessel time constant τ of the pulmonary arterial tree is then determined from this impulse response by fitting an exponential to its tail end once the faster wave and inertial effects have vanished (h(t) in FIG. 5). Finally, proportional CO is determined as the difference between the mean value of the analyzed PAP waveform segment and average LAP (i.e., the resulting constant term) divided by the resulting τ. Alternatively, when the area of each impulse of the cardiac contractions signal is set to an arbitrary constant, proportional CO may be determined as the product of the peak value of the pulmonary arterial tree impulse response and the average heart rate.

The above aspects of the present invention may be utilized, for example, in patients instrumented with pulmonary artery catheters in ICUs, ORs, and recovery rooms. In such applications, the continuous, proportional CO, PVR, and/or τ values may be conveniently calibrated to continuous, absolute CO and PVR values with a single thermodilution measurement. It will be appreciated that certain embodiments of the invention provide absolute average LAP without requiring calibration based on a thermodilution measurement.

Preferred methods of the invention for determining proportional CO, average LAP, proportional PVR, and/or other clinically important hemodynamic variables by performing a mathematical analysis of a PAP waveform, e.g., as described above, do not entail the use of a neural network. Certain preferred methods of the invention also do not make use of a set of training data. For example, the methods of the invention for determining proportional CO, average LAP, proportional PVR, and/or other clinically important hemodynamic variables do not require making conventional measurements of a subject's PCWP (e.g., by advancing a pulmonary artery catheter into a branch of the pulmonary artery, inflating the balloon, and averaging the ensuing steady-state pressure) as a prerequisite to the monitoring of proportional CO, average LAP, and/or other clinically important hemodynamic variables in the subject. The methods of the invention for determining proportional CO, average LAP, proportional PVR, and/or other clinically important hemodynamic variables also do not require a training data set comprising conventional measurements of PCWP in one or more subjects in order to monitor, according to the methods of the invention, proportional CO, average LAP, and/or other clinically important hemodynamic variable(s) in the same subjects or different subjects.

It will thus be appreciated that the methods described above provide a means of determining LAP and/or other clinically important hemodynamic variables based on first principles rather than estimating or determining PCWP and then using the estimated or determined PCWP as an approximation to LAP. In preferred embodiments, the methods and apparatus of the invention are therefore not adapted specifically for determining PCWP from a PAP waveform based on a correlation between measured values of the PAP and PCWP but instead determine LAP without relying on a correlation between measured PAP and PCWP. As mentioned above, in practice PCWP is usually measured primarily in order to provide an estimate of LAP even though such an estimate suffers from a number of limitations noted above. Thus, the methods of the invention offer an advantage over prior art methods that employ either a measured or estimated PCWP value as an estimate for LAP. However, if desired, the LAP determined according to the methods of the invention could be used to approximately determine PCWP. That is, LAP determined according to the methods of the invention could either be used directly as an approximate of PCWP, or the determined LAP could be adjusted in order to provide an improved estimate of PCWP. For example, in one embodiment, such an adjustment is accomplished through a training data set comprising PAP waveforms and conventional PCWP measurements. More specifically, LAP is determined as described above with respect to the PAP waveforms in the training data set, and a model (e.g., linear or nonlinear regression) is developed according to any of the methods known in the art to predict the corresponding PCWP measurements in the training data set. Then, PCWP is subsequently estimated from a PAP waveform by first determining LAP according to the methods of the invention and then applying the trained model to the determined LAP to predict PCWP.

In yet another such embodiment, proportional CO, average LAP, and/or other hemodynamic variables such as proportional PVR are determined by mathematical analysis of the contour of a RVP waveform. The RVP waveform is preferably obtained from patients without stenosis of the pulmonic valve so that the RVP waveform may be regarded as equivalent to the unobserved PAP waveform during each systolic ejection interval. The systolic ejection intervals of the RVP waveform are identified by any method known in the art, e.g., using a phonocardiogram or other physiologic signals. For example, the beginning of systole for each beat may be determined as the time of the maximum temporal derivative of each RVP pulse [61], while the end of systole for each beat may be identified as the time of the peak value of each RVP pulse (y(t) in FIG. 6a). Then, with this "incomplete" PAP waveform, also referred to as a "partial" PAP waveform herein, the clinically significant hemodynamic variables may be determined similarly to the embodiments described above. For example, the systolic ejections intervals of a segment of a RVP waveform of duration greater than a cardiac cycle (e.g., ranging from 30 seconds to ten-minutes) are fitted according to the sum of an unknown constant term representing the average LAP and the convolution of an unknown impulse response representing the dynamical properties of the pulmonary arterial tree with a known and complete cardiac contractions signal as defined above. The impulse response and constant term that provide the best fit of the systolic ejection intervals of the RVP waveform segment (based on any method known in the art) are then utilized to determine average LAP and the Windkessel time constant $\tau$ of the pulmonary arterial tree as described above (FIG. 6a). Next, the complete PAP waveform segment (including diastolic intervals) is constructed by the convolution between the resulting impulse response and the complete cardiac contractions signal (z(t) in FIG. 6b) plus the resulting average LAP. Finally, proportional CO is determined either as the difference between the mean value of the constructed PAP waveform segment and the resulting average LAP divided by the resulting $\tau$ or the product of the peak value of the pulmonary arterial tree impulse response and the average heart rate. This particular aspect of the invention may be utilized, for example, in patients instrumented with implanted devices capable of monitoring a RVP waveform [1].

The method (and apparatus) for constructing a PAP waveform containing both systolic and diastolic intervals based on the systolic ejection intervals of the RVP waveform is an aspect of this invention. The PAP waveform constructed according to the method of the invention can be further analyzed for any of a variety of purposes including, but not limited to, determining average LAP, proportional CO, or proportional PVR as described herein.

In another embodiment of the invention, the mathematical analysis of a circulatory contour involves the use of a Windkessel model analogous to FIG. 3 to represent the slow dynamical properties of the systemic arterial tree. In one such embodiment, the above mathematical procedures described in the context of PAP waveform analysis are applied to a SAP waveform (or a related waveform such as a photoplethysmography signal) measured at any site in the systemic arterial tree. Similarly, the above mathematical procedures described in the context of RVP waveform analysis may be applied to a left ventricular pressure (LVP) waveform in which aortic stenosis is absent. In such embodiments, the dynamical properties of the systemic arterial tree and the average SVP (through the constant term) are determined. Alternatively, SVP may be regarded as negligible with respect to SAP (i.e., left panel of FIG. 1) and only the dynamical properties of the systemic arterial tree are determined. The determined dynamical properties may then be analogously utilized to determine proportional CO and proportional SVR. These particular aspects of the invention may be utilized, for example, in ICUs, ORs, and recovery rooms in which radial artery catheters are routinely employed or at home, in emergency rooms, and in the ward in which non-invasive SAP waveforms (e.g., finger-cuff photoplethysmography [32], arterial tonometry [35]) could easily be obtained. The continuous, proportional CO and $\tau$ values may be conveniently calibrated to continuous, absolute CO and SVR values with a single, absolute measurement of CO.

The method for constructing a SAP waveform containing both systolic and diastolic intervals based on the systolic ejection intervals of the LVP waveform is an aspect of this invention. The SAP waveform constructed according to the method of the invention can be further analyzed for any of a variety of purposes including, but not limited to, determining SVP, proportional CO, or proportional SVR as described herein.

In any of these embodiments, the constant term represents the asymptotic value of the waveform were cardiac contractions to cease. Thus the invention provides a method for determining the value of a hemodynamic variable based on a PAP, RVP, SAP, or LVP waveform, comprising steps of (i) performing a mathematical analysis to determine the asymptotic value of the waveform were cardiac contractions to cease and (ii) selecting the asymptotic value as the value for the hemodynamic variable. In certain embodiments of the invention the waveform is a PAP waveform and the hemodynamic variable is average LAP. In certain embodiments of the invention the waveform is a RVP waveform and the hemodynamic variable is average LAP. In certain embodiments of the invention the waveform is a SAP waveform and the hemodynamic variable is average SVP. In certain embodiments of the invention the waveform is a LVP waveform and the hemodynamic variable is average SVP. Any of the methods may further comprise determining the value of proportional CO, proportional PVR, or proportional SVR.

The invention further comprises apparatus for use in performing any one or more of the methods of the invention.

The invention further provides computer-executable process steps stored on a computer-readable medium for performing one or more methods of the invention. The invention further provides methods of monitoring a subject comprising performing one or more of the inventive methods on a PAP waveform, RVP waveform, SAP waveform or related signal, or LVP waveform obtained from the subject. The methods may further comprise the step of obtaining such a waveform from the subject. The methods may further comprise the step of administering a therapy to the subject, or modifying the subject's therapy, based on one or more hemodynamic variables obtained according to the methods.

DETAILED DESCRIPTION OF CERTAIN EMBODIMENTS OF THE INVENTION

The present invention is based at least in part on the recognition that proportional CO, average LAP, and/or other hemodynamic variables are reflected in the contour of a PAP waveform, a RVP waveform, or other circulatory signals. The invention therefore involves the mathematical analysis of the contour of a circulatory signal so as to decipher, and thereby determine, e.g., continuously, these clinically significant hemodynamic variables. The mathematical analysis of a circulatory contour is specifically defined here to comprise an examination of the temporal variations in the signal. Thus, for example, monitoring LAP via the end-diastolic PAP does not constitute a mathematical analysis of a circulatory contour, since this examination simply indicates PAP at particular instances of time (end-diastole).

Figure 1:
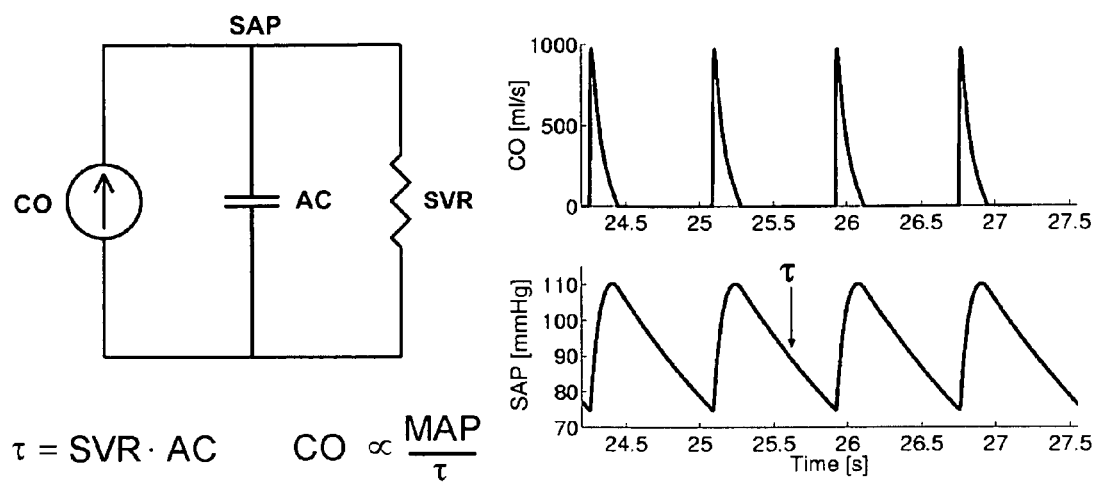
FIG. 1: Previous analysis technique for monitoring cardiac output (CO) from a systemic arterial pressure (SAP) waveform [6]. According to the Windkessel model of the systemic arterial tree (electrical analog to the left), SAP should decay like a pure exponential during each diastolic interval with a time constant ($\tau$) equal to the product of the systemic vascular resistance (SVR) and the nearly constant arterial compliance (AC). Thus, this technique involves first fitting an exponential function to each diastolic interval of the SAP waveform to determine $\tau$ (right) and then dividing the time-averaged SAP (MAP) with $\tau$ to estimate proportional CO.
Figure 2:
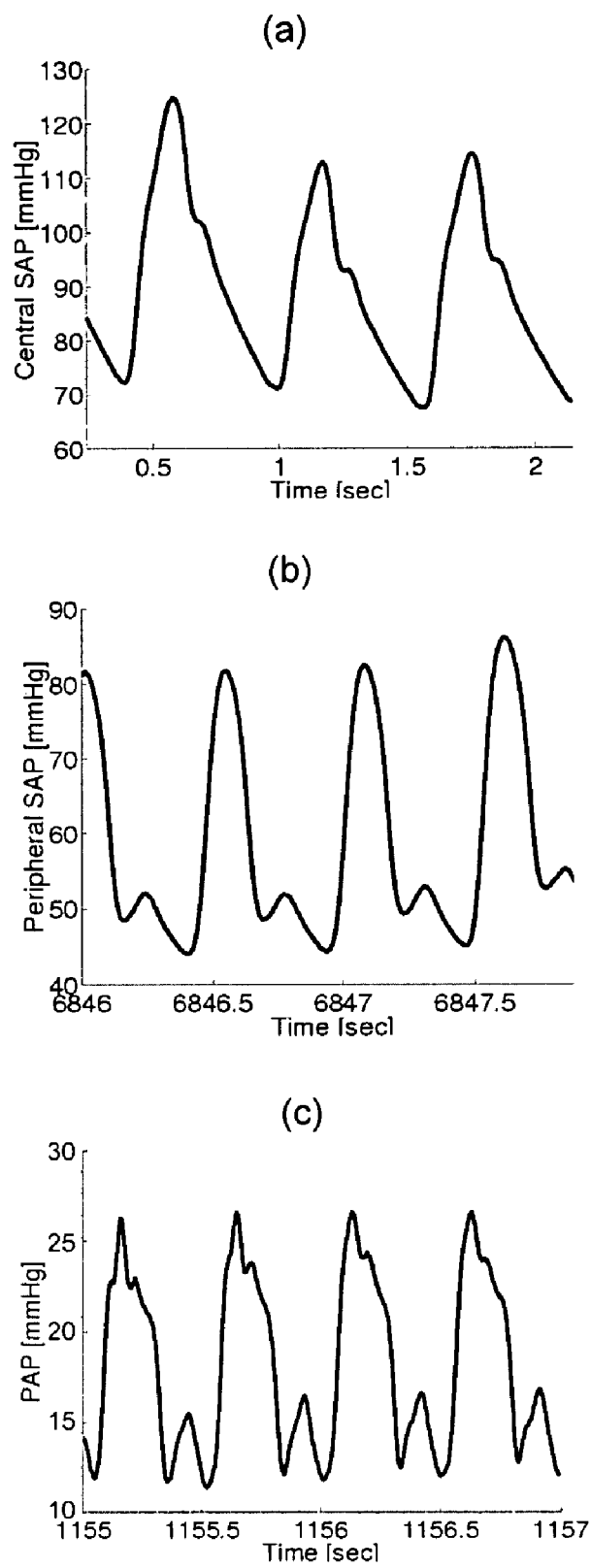
FIG. 2: Swine arterial pressure waveforms measured a) centrally in the aorta, (b) peripherally in the radial artery, and (c) in the main pulmonary artery. The diastolic intervals of the central systemic arterial pressure (SAP) waveform resemble exponential decays; however, the measurement of central SAP is too invasive for routine clinical application. In contrast, exponential diastolic decays are not visible in the peripheral SAP and pulmonary artery pressure (PAP) waveforms, which are heavily corrupted by fast wave reflections and inertial effects. Thus, the previous technique in FIG. 1 cannot be applied to clinically measurable peripheral SAP and PAP waveforms.
Figure 3:
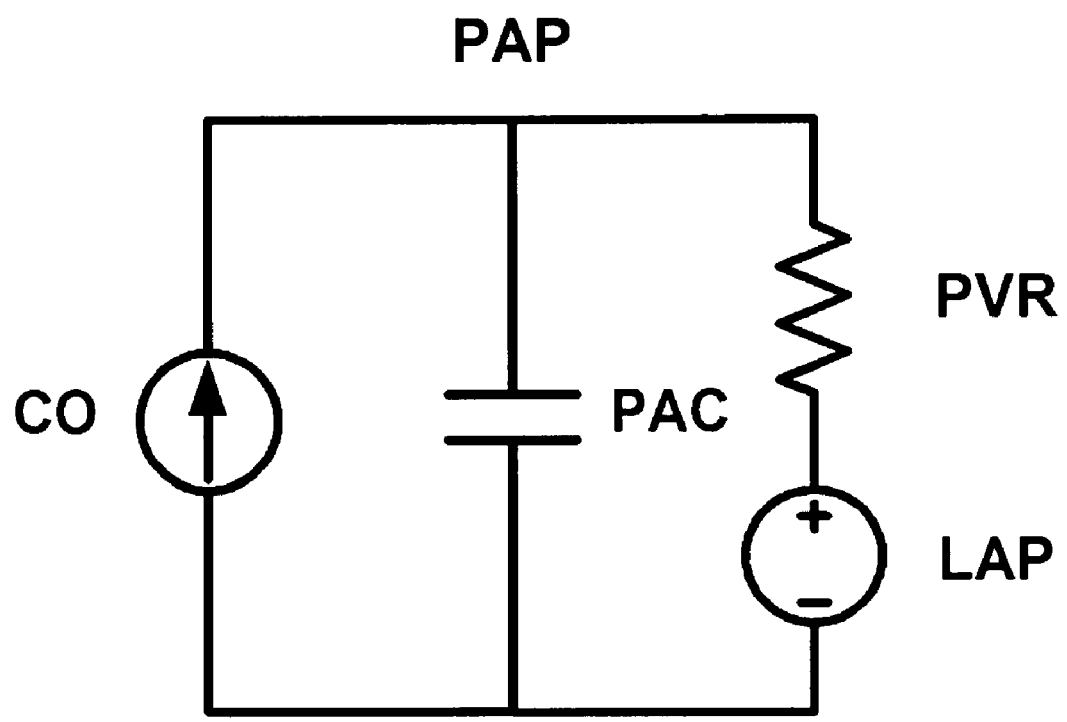
FIG. 3: Electrical analog of the Windkessel model of the pulmonary arterial tree. One embodiment of the mathematical analysis utilizes this model to represent the slow dynamical behavior of the pulmonary arterial tree. For example, if pulsatile activity suddenly ceased, this model predicts that pulmonary artery pressure (PAP) would eventually decay like a pure exponential with a Windkessel time constant $\tau$ equal to the product of the pulmonary vascular resistance (PVR) and the nearly constant pulmonary arterial compliance (PAC) as soon as the faster wave and inertial effects vanished (see FIG. 2). The model also indicates that the exponential pressure decay would equilibrate towards the left atrial pressure (LAP), which significantly contributes to PAP due to the relatively small PVR.

In one embodiment of the invention, the mathematical analysis of a circulatory contour is based on the Windkessel model of the pulmonary arterial tree shown in FIG. 3. (Although PVR is known to be nonlinear over a wide pressure range [25], it may be approximated as linear over the more narrow range of PAP variations that are considered by various embodiments of the present invention.) According to this model, PAP should decay like a pure exponential during each diastolic interval with a time constant ($\tau$) equal to the product of PVR and the pulmonary AC (PAC). The model further indicates that the exponential pressure decay should equilibrate towards average LAP rather than zero pressure. Thus, the Windkessel model of FIG. 3 suggests that both $\tau$ and average LAP may be determined from a PAP waveform by fitting a single exponential function plus a constant term to each of its diastolic intervals. Moreover, since PAC may be nearly constant over a wide pressure range, CO may also be determined to within a constant scale factor by dividing the time-averaged PAP-LAP with $\tau$. However, the invention encompasses the recognition that this simple fitting procedure is not generally valid in practice, because exponential diastolic decays are usually obscured in physiologic PAP waveforms by complex wave and inertial effects (FIG. 2c). To determine the Windkessel parameters (τ and average LAP) from a PAP waveform, the invention further encompasses the recognition that the confounding wave and inertial dynamics are faster than the exponential Windkessel dynamics [55]. This implies that if pulsatile activity were to abruptly cease, then PAP would eventually decay like a pure exponential and ultimately equilibrate to the LAP once the faster wave and inertial dynamics vanished. Thus, in this embodiment, the Windkessel model of FIG. 3 is specifically used to represent only the slow dynamical properties of the pulmonary arterial tree.

Figure 4:
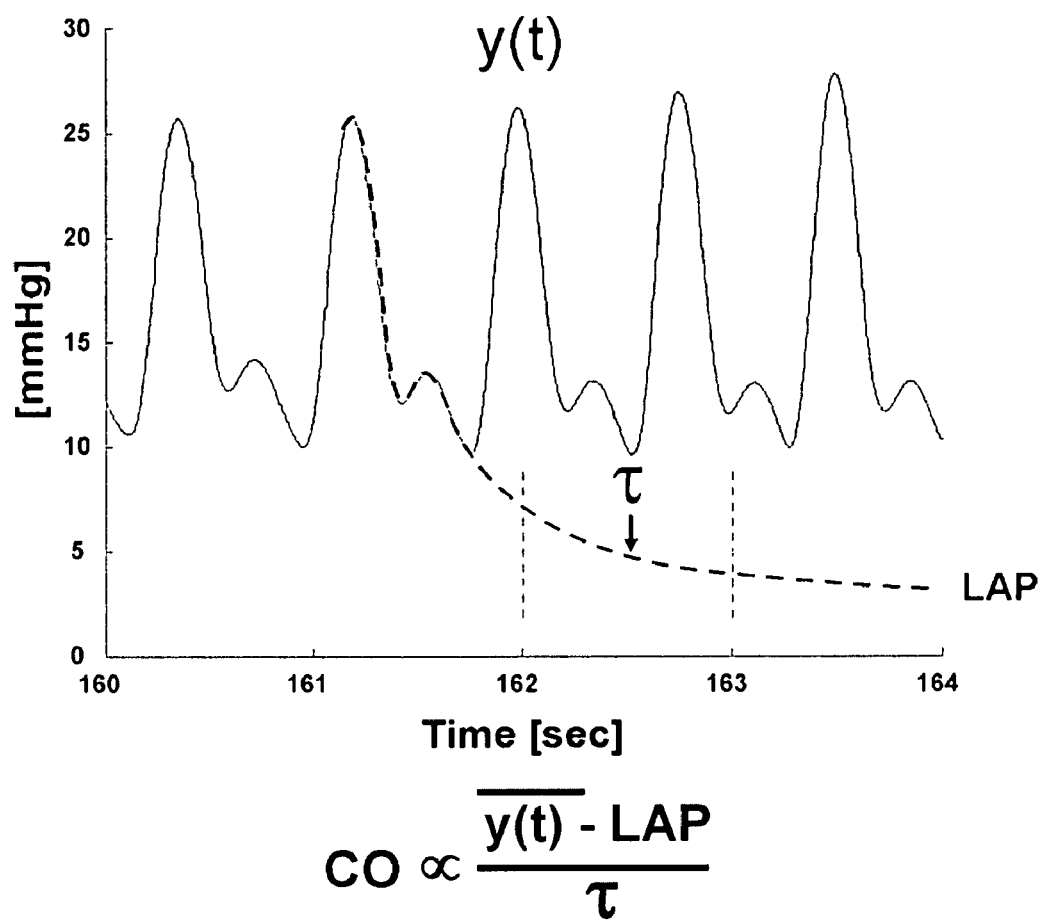
FIG. 4: One embodiment in which the mathematical analysis is applied to the individual diastolic decay intervals of a pulmonary artery pressure (PAP) waveform (y(t)). Multiple, complex exponential functions and a constant term are fitted to each diastolic decay interval of y(t) to respectively determine the dynamical properties of the pulmonary arterial tree and the average left atrial pressure (LAP). Then, the Windkessel time constant $\tau$ of the pulmonary arterial tree (see FIG. 3) is determined by extrapolating the computed exponential functions to low-pressure values and fitting a mono-exponential function to the extrapolated pressure values for which the faster wave and inertial effects have vanished. Finally, proportional cardiac output (CO) is determined via Ohm's law (overbar indicates time averaging). This intra-beat embodiment of the mathematical analysis may be capable of monitoring beat-to-beat changes in CO and LAP.

In one such embodiment, proportional CO, average LAP, and/or other hemodynamic variables are determined by mathematical analysis of each individual diastolic decay interval of a PAP waveform. For example, basis functions, e.g., multiple, complex exponential functions and a constant term are fitted to each diastolic decay interval of PAP to respectively determine the dynamical properties of the pulmonary arterial tree and the average LAP (FIG. 4). Then, the Windkessel time constant τ of the pulmonary arterial tree may be determined by extrapolating the computed exponential functions to low-pressure values and fitting a mono-exponential function to the extrapolated pressure values for which the faster wave and inertial effects have dissipated (FIG. 4). Finally, proportional CO may be determined over any number of beats via Ohm's law.

FIG. 4 illustrates the details of this embodiment of the mathematical analysis, which is applied to a digitized PAP waveform sampled at, for example, 90 Hz. It will be appreciated that different sampling rates could be used. This embodiment is specifically employed in four steps.

First, the diastolic decay interval of each PAP pulse is identified as the entire downstroke (i.e., from maximum to minimum pressure) or by any other method known in the art. For example, each diastolic decay interval may be identified with a simultaneous phonocardiogram measurement. As another example, each diastolic decay interval may be determined according to any formula based on the cardiac cycle length (T) such as the well-known Bazett formula (T−0.3√T) [4]. Each cardiac cycle length may be determined from the PAP waveform and/or other simultaneously measured physiologic signals such as a surface ECG measurement.

Second, any number of complex exponential functions and a constant term are fitted to each of the identified diastolic decay intervals of the PAP waveform (v(t)). The estimated constant term represents the average LAP, while the estimated complex exponential functions characterize the wave, inertial, and Windkessel dynamical properties of the pulmonary arterial tree. The "best" fit complex exponential functions and constant term may be specifically estimated based on the following output error equation with constant term c and unit impulse (δ(t)) input:

$$h(t) = \sum_{k=1}^{n} a_k h(t-k) + \sum_{k=1}^{n} b_k \delta(t-k) \quad (1)$$

$$y(t) = c + h(t) + e(t).$$

Here, e(t) is the unmeasured residual error, the pair of parameters $\{a_k, b_k\}$ completely specify each complex exponential function, n indicates the number of complex exponential functions, and h(t) represents the temporal evolution of the complex exponential functions collectively for all time. For a given value of n, the parameters including c are estimated from the diastolic decay intervals of y(t) through the least-squares minimization of the residual error [43]. This optimization problem may be solved through a numerical search (e.g., Gauss Newton method) or the Stieglitz-McBride iteration [43]. Alternatively, the parameters may be more conveniently, but not optimally, estimated using other methods known in the art such as Prony's method and Shank's method [7,56]. A pre-determined number of complex exponential functions (usually an odd number such as n=1, 3 or 5) may be utilized in the estimation procedure. Alternatively, an optimal number of complex exponential functions may be determined according to any of the methods known in the art that penalize for unnecessary parameters (e.g., root-normalized-mean-squared-error (RNMSE) threshold) [43]. Prior to this estimation procedure, y(t) may be lowpass filtered in order to attenuate the complex wave and inertial effects. Note that any other parametric model with complex exponential basis functions (e.g., autoregressive exogenous input (ARX) model [43]) or any other functions (e.g., polynomials) may be employed in various embodiments of the invention to represent the diastolic decay interval of each PAP pulse, and any other minimization criterion (e.g., absolute error) may be utilized to determine the "best" fitting functions and constant term. It will be appreciated that it is not necessary to select the parameters that in fact result in minimizing the error, although these parameters may provide the most accurate results. Instead, the parameters can be selected such that the error is below a predetermined value (e.g., 110-120% of the minimum error), in which the predetermined value is specifically selected so as to achieve an acceptable accuracy for the purposes at hand.

Third, the estimated complex exponential functions are extrapolated to low-pressure values. This step is achieved by recursively solving for h(t) (until it is effectively zero) based on the estimated parameters $\{\hat{a}_k, \hat{b}_k\}$ as follows:

$$h(t) = \sum_{k=1}^{n} \hat{a}_k h(t-k) + \sum_{k=1}^{n} \hat{b}_k \delta(t-k). \quad (2)$$

The Windkessel time constant τ of the pulmonary arterial tree is then determined over the interval of h(t) preferably over a time interval in which the faster wave and inertial effects have become minimal. For example, as shown in FIG. 4, the contribution of the faster wave reflections and inertial effects becomes minimal within one second of the peak value of h(t). Following this time interval, h(t) may be accurately approximated as a mono-exponential. Thus, in certain preferred embodiments of the invention, the selected time interval begins approximately 0.75 seconds following the time of maximum h(t) or, more preferably, approximately one second following the time of maximum h(t). For example, it has been found that a time interval of 1 to 2 seconds following the time of maximum value of h(t) is suitable. Longer time intervals may also be used. Typically the appropriate time interval is predetermined, but, in certain embodiments of the invention, it may be selected as the measurements are being made. The determination of τ is achieved based on the selected interval of h(t) according to the following single exponential equation:

$$h(t) = Ae^{-t/\tau} + w(t). \quad (3)$$

The parameters A and τ may be estimated according to any procedure known in the art. For example, the parameters may be determined by the closed-form, linear least squares solution after log transformation of h(t). Alternatively, $\tau$ may be identified as the largest real valued time constant of the estimated complex exponential functions. Note that this step is unnecessary when only a single exponential function is utilized to fit the diastolic decay interval of the PAP pulse.

Finally, the average LAP is determined as the mean or median value of the estimated constant term $\hat{c}$ over any number of beats, while CO is determined to within a constant scale factor equal to 1/PAC as the difference between the mean value of PAP over any number of beats and the corresponding average LAP divided by the mean or median value of the corresponding $\tau$. Note that PVR is also trivially determined to within a constant scale factor via $\tau$. The proportional, continuous CO and PVR estimates may be calibrated, if desired, with a single, absolute measurement of CO. Such a calibration may be conveniently implemented with the bolus thermodilution method, if a pulmonary artery catheter were employed. Otherwise, if an independent CO measurement is unavailable, then a nomogram may be utilized, if desired, to calibrate the proportional estimates.

Figure 5:
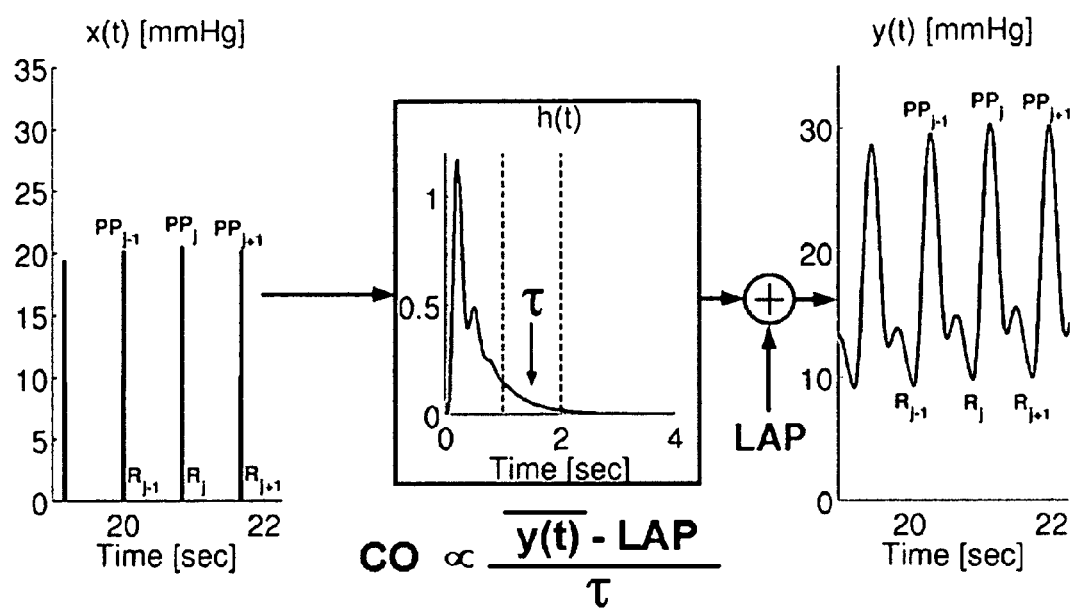
FIG. 5: One embodiment in which the mathematical analysis is applied to all temporal variations in a pulmonary artery pressure (PAP) waveform (y(t)) including those occurring over time scales greater than a cardiac cycle. Average left atrial pressure (LAP) and the response of PAP minus average LAP to a single, solitary cardiac contraction (h(t)) are simultaneously estimated by fitting a segment of y(t). Then, the Windkessel time constant $\tau$ of the pulmonary arterial tree (see FIG. 3) is determined by fitting a mono-exponential function to the tail end of h(t) once the faster wave and inertial effects have vanished. Finally, proportional cardiac output (CO) is computed via Ohm's law (overbar indicates time averaging). This inter-beat embodiment of the mathematical analysis is expected to be able to accurately determine average $\tau$ and LAP, because beat-to-beat PAP variations are hardly confounded by wave and inertial phenomena [55]. PP is pulse pressure; R, the time of the onset of upstroke of each PAP pulse; j, the $j^{th}$ beat; x(t), an impulse train signal representing cardiac contractions.

Alternatively, proportional CO, average LAP, and other hemodynamic variables are determined by mathematical analysis of all temporal variations in a PAP waveform including those occurring over time scales greater than a cardiac cycle in which the confounding effects of wave and inertial phenomena are attenuated [55]. For example, average LAP and the response of PAP minus average LAP to a single, solitary cardiac contraction (h(t) in FIG. 5) are simultaneously estimated by fitting a PAP waveform segment of duration greater than a cardiac cycle (e.g., 30 seconds to 10 minutes). Then, the Windkessel time constant $\tau$ of the pulmonary arterial tree is determined by fitting a mono-exponential function to the tail end of h(t) once the faster wave and inertial effects have vanished (FIG. 5). Finally, proportional CO may be computed by dividing the time-averaged PAP-LAP with $\tau$. Without wishing to be bound by any theory, while an intra-beat embodiment will likely provide better temporal resolution (e.g., ability to detect beat-to-beat hemodynamic changes), an inter-beat embodiment is expected to be more accurate in terms of estimating average hemodynamic values as the beat-to-beat PAP variations are much more reflective of Windkessel dynamics than confounding wave and inertial phenomena (i.e., a larger signal-to-"noise" ratio) [55].

FIG. 5 illustrates the details of this embodiment of the mathematical analysis, which is applied to a segment of a digitized PAP waveform (sampled at, e.g., 90 Hz) of duration greater than a cardiac cycle (e.g., 30 seconds to ten minutes). It will be appreciated that different sampling rates could be used. This embodiment is specifically employed in four steps.

First, a cardiac contractions signal is constructed by forming an impulse train in which each impulse is located at the onset of upstroke of a PAP pulse (R) and has an area equal to the ensuing pulse pressure (PP). PP is determined, for example, as the maximum PAP value minus the PAP value at the onset of upstroke. Alternatively, each impulse may be placed at the R-wave of a simultaneous surface ECG measurement, and/or the area of each impulse may be set to an arbitrary constant or any other value based on the PAP pulse. As another alternative, pulses of any shape (e.g., rectangular) with duration equal to the systolic ejection interval (as determined above) may be utilized in lieu of the transient impulses.

Second, the relationship between the cardiac contractions signal (x(t)) and the PAP waveform segment (y(t)) is determined by estimating both a constant term and an impulse response (h(t)) which when convolved with x(t) "best" fits y(t) minus the constant term. The estimated constant term represents the average LAP, while the estimated h(t) characterizes the dynamical properties of the pulmonary arterial tree and is defined to represent the (scaled) PAP-LAP response to a single cardiac contraction. The impulse response h(t) and average LAP may be specifically estimated according to the following ARX equation with constant term c:

$$y(t) = c + \sum_{k=1}^{m} a_k y(t-k) + \sum_{k=1}^{n} b_k x(t-k) + e(t), \quad (4)$$

where e(t) is the unmeasured residual error, the parameters $\{a_k, b_k\}$ completely specify h(t), and m and n limit the number of these parameters (model order) [43]. For a fixed model order, the parameters including c are estimated from x(t) and y(t) through the least-squares minimization of the residual error, which has a closed-form solution [43]. The model order is determined by minimizing any criterion (e.g., Minimum Description Length criterion) or method known in the art that penalizes for unnecessary parameters [43]. Prior to this estimation procedure, x(t) and y(t) may be lowpass filtered in order to amplify the contribution of long time scale energy such that the least squares estimation is prioritized at these time scales. With the estimated parameters $\{\hat{a}_k, \hat{b}_k\}$ and $\hat{c}$, average LAP and h(t) are computed as follows:

$$LAP = \hat{c} \bigg/ \left(1 - \sum_{k=1}^{m} \hat{a}_k\right) \quad (5)$$

$$h(t) = \sum_{k=1}^{n} \hat{a}_k h(t-k) + \sum_{k=1}^{n} \hat{b}_k \delta(t-k). \quad (6)$$

Note that any other parametric model (e.g., autoregressive moving average with exogenous input (ARMAX) equation [43]) may be employed in various embodiments of the invention to represent the structure of h(t), and any other minimization criterion (e.g., absolute error) may be utilized to determine the "best" h(t) and average LAP.

Third, the Windkessel time constant $\tau$ of the pulmonary arterial tree is determined over the interval of h(t) for which the faster wave and inertial effects have dissipated For example, the interval ranging from one to two seconds following the time of the maximum value of h(t) may be selected. (See FIG. 5 and discussion above for other exemplary time intervals.) This step may be achieved based on Equation (3) as described above. Thus, in certain embodiments of the invention, accurate determination of $\tau$ as well as LAP are achieved by virtue of h(t) coupling the long time scale variations in x(t) to y(t)-LAP.

Finally, proportional CO is computed via Ohm's law, and proportional PVR is given as $\tau$. Alternatively, when the area of each impulse in x(t) is set to an arbitrary constant value, proportional CO may be determined as the product of the peak value of the estimated h(t) and the average heart rate and proportional PVR may be subsequently determined via Ohm's law. The proportional, continuous CO and PVR estimates may be calibrated, if desired, as described above.

The aforementioned embodiments of the mathematical analysis may also be applied to a SAP waveform (or a related waveform such as a photoplethysmography signal) measured at any site in the systemic arterial tree. In this way, proportional CO, proportional SVR, and average SVP or only proportional CO and proportional SVR (with SVP assumed to be negligible, i.e., c=0) may be continuously monitored.

Figure 6:
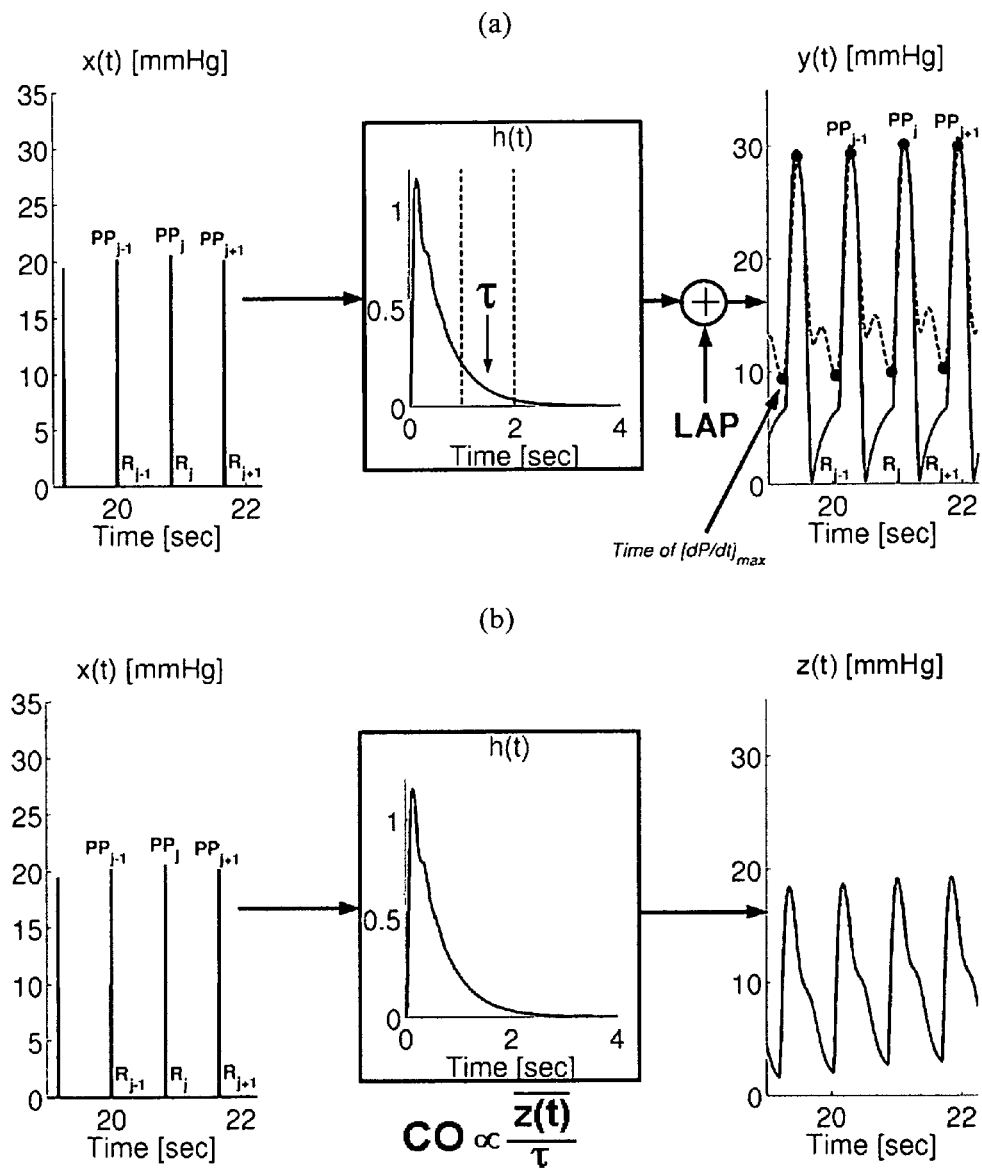
FIG. 6: One embodiment in which the mathematical analysis is applied to a right ventricular pressure (RVP) waveform (y(t)) obtained from patients without pulmonic valve stenosis. (a) The systolic ejection intervals of a RVP waveform segment are identified and regarded as equivalent to the unobserved pulmonary artery pressure (PAP). Then, average left atrial pressure (LAP) and the response of PAP minus average LAP to a single, solitary cardiac contraction (h(t)) are simultaneously estimated by fitting the incomplete segment of y(t). Next, the Windkessel time constant $\tau$ of the pulmonary arterial tree (see FIG. 3) is determined by fitting a mono-exponential function to the tail end of h(t) once the faster wave and inertial effects have vanished. (b) Finally, the complete PAP-LAP waveform segment (including diastolic intervals) is constructed (z(t)), and proportional cardiac output (CO) is determined via Ohm's law (overbar indicates time averaging). PP is pulse pressure; R, the time of the onset of upstroke of each PAP pulse; j, the $j^{th}$ beat; x(t), an impulse train signal representing cardiac contractions.

In another embodiment, proportional CO, average LAP, and other hemodynamic variables are determined by mathematical analysis of the contour of a RVP waveform. A key idea of this aspect of the invention is that RVP and PAP may be regarded as nearly equal during the systolic ejection interval of each beat provided that there is no significant stenosis of the pulmonic valve (FIG. 6). The systolic ejection intervals of the observed RVP waveform are therefore identified so as to produce an "incomplete" PAP waveform without diastolic pressure information. Then, with this incomplete PAP waveform, the clinically significant hemodynamic variables may be determined similarly to embodiments described above.

For example, FIG. 6 illustrates one such embodiment of the mathematical analysis, which is applied to a segment of a digitized RVP waveform (sampled at, e.g., 90 Hz) of duration greater than a cardiac cycle (e.g., 30 seconds to ten minutes). This particular embodiment is employed in six steps.

First, each systolic ejection interval within the RVP waveform segment is identified. The beginning of systole for each beat is determined as the time of the maximum temporal derivative of each RVP pulse [61], while the end of systole for each beat is identified as the time of the peak value of each RVP pulse. Alternatively, any other method known in the art (e.g., see above) may be used to identify the systolic ejection intervals. This step produces an incomplete segment of a PAP waveform.

Second, a cardiac contractions signal is constructed as described above. Note that the resulting cardiac contractions signal is defined for all values of time (i.e., both systole and diastole).

Third, the relationship between the complete cardiac contractions signal ($x(t)$) and the incomplete PAP waveform ($y(t)$) is characterized by estimating both a constant term representing average LAP and the impulse response ($h(t)$) which when convolved with $x(t)$ "best" fits $y(t)$ minus the average LAP. The impulse response $h(t)$ and average LAP may be specifically estimated according to the following output error equation with constant term c:

$$w(t) = \sum_{k=l}^{m} a_k w(t-k) + \sum_{k=l}^{n} b_k x(t-k) \quad (7)$$
$$y(t) = w(t) + c + e(t).$$

Again, $e(t)$ is the unmeasured residual error, the parameters $\{a_k, b_k\}$ completely specify $h(t)$, and m and n limit the number of these parameters (model order) [43]. For a fixed model order, the parameters including c are estimated from $x(t)$ and the incomplete $y(t)$ through the least-squares minimization of the residual error during the systolic ejections intervals. This optimization problem may be solved, for example, through a numerical search procedure (e.g., Gauss Newton method) or the Stieglitz-McBride iteration [43]. The model order may be determined similarly to that of Equation (1). Prior to this estimation procedure, $x(t)$ and $y(t)$ may be lowpass filtered in order to amplify the contribution of long time scale energy such that the least squares estimation is prioritized at these time scales. With the estimated parameters $\{\hat{a}_k, \hat{b}_k\}$ and $\hat{c}$, $h(t)$ is computed according to Equation (6) and average LAP is given as $\hat{c}$. Note that other parametric models may be employed in various embodiments of the invention to represent the structure of $h(t)$, and any other minimization criterion (e.g., absolute error) may be utilized to determine the "best" $h(t)$ and average LAP. However, some methods known in the art may be less preferable (e.g., linear least squares identification of ARX models), since the output is not known for all time here.

Fourth, $\tau$ is determined from the estimated $h(t)$ based on Equation (3) as described above. Again, in certain embodiments of the invention, accurate determination of $\tau$ as well as average LAP is achieved by virtue of $h(t)$ coupling the long time scale variations in $x(t)$ to the incomplete $y(t)$-LAP.

Fifth, the complete PAP waveform including diastolic information is constructed by convolving the cardiac contractions signal $x(t)$ with the estimated $h(t)$ and then summing this response ($z(t)$) to the average LAP. This step is mathematically achieved as follows:

$$w(t) = \sum_{k=l}^{m} \hat{a}_k w(t-k) + \sum_{k=l}^{n} \hat{b}_k x(t-k) \quad (8)$$
$$y(t) = w(t) + \hat{c}.$$

Finally, proportional CO is determined via Ohm's law, and proportional PVR is trivially obtained with $\tau$. Alternatively, when the area of each impulse in $x(t)$ is set to an arbitrary constant value, proportional CO may also be determined as the product of the peak value of the estimated $h(t)$ and the average heart rate and proportional PVR may be subsequently determined via Ohm's law. Again, if desired, the proportional, continuous CO and PVR estimates may be calibrated as described above. This embodiment of the invention may also be applied to LVP waveforms in order to continuously monitor proportional CO, proportional SVR, and average SVP or only proportional CO and proportional SVR (with SVP assumed to be negligible, i.e., c=0). The invention includes apparatus for performing the methods described above, e.g., for determining LAP. For example, the apparatus may comprise memory means that stores a program comprising computer-executable process steps and a processing unit that executes the computer-readable process steps so as to perform a mathematical analysis of the contour of a PAP waveform, RVP waveform, SAP waveform, LVP waveform or another circulatory signal (or any two or more of the foregoing) and uses the mathematical analysis to determine average LAP, proportional CO, proportional PVR, proportional SVR, average SVP, etc. The apparatus may perform any one or more of the methods described herein to determine any one or more of the hemodynamic variables discussed herein, e.g., average LAP, proportional CO, proportional PVR, proportional SVR, average SVP.

In certain embodiments of the present invention, an analog PAP waveform, RVP waveform, SAP waveform, LVP waveform or another circulatory signal is fed into an analog-to-digital converter as it is being measured. The circulatory signal may be acquired using standard methods, such as those mentioned above. In certain embodiments of the invention, a surface ECG is also measured, e.g., via standard ECG leads. The digitized circulatory signal and the ECG, if measured, are stored in a buffer system. The most recent time intervals of the digitized signals (e.g., one cardiac cycle to ten minutes) are transferred from the buffer system to a processing unit, which analyzes the signal according to the methods of the invention. The buffer and processing unit may be implemented using, for example, any standard microcomputer or implanted circulatory monitoring device running appropriate software to implement the mathematical operations described above. The software components of the invention may be coded in any suitable programming language and may be embodied in any of a range of computer-readable media including, but not limited to, floppy disks, hard disks, CDs, zip disks, DVD disks, etc. It will be appreciated that the term "processing unit" is used herein to refer to any suitable combination of general and/or special purpose processors. For example, at least some of the processing steps may be implemented using hardware, e.g., signal processing chips. Thus the methods may be implemented using any suitable combination of general and/or special purpose processors and appropriate software. Computer-readable media that store computer-executable process steps to perform all or part of one or more methods of the invention are also an aspect of the invention.

Outputs such as proportional CO, LAP or SVP, and proportional PVR or SVR may be displayed on a visual display such as a computer screen and/or may be printed or transmitted to a remote location. The ECG, and analysis thereof, may also be displayed. In a preferred embodiment of the system, the process is continuously repeated thereby providing the on-line monitoring of proportional CO, LAP or SVP, proportional PVR or SVR, and/or other hemodynamic variables (e.g., with a delay equal to half the selected analysis interval). Alternatively or additionally, absolute CO and PVR or SVR may be computed and displayed through a nomogram or a single, independent measurement of absolute CO. In certain embodiments of the invention, an alarm is triggered upon excessive changes in any of the estimated variables.

Finally, the methods may further comprise the step of selecting, recommending, suggesting, or administering a therapy to the subject, or modifying the subject's therapy, based on values for one or more hemodynamic variables obtained according to the methods and apparatus. The therapy may be, for example, any medical or surgical therapy known in the art that is suitable for treating a subject having a physiological state consistent with the determined average LAP, average SAP, proportional CO, proportional PVR and/or proportional SVR. Exemplary therapies include pharmaceutical agents, e.g., pressors or diuretics, fluids, etc. In certain embodiments of the invention therapy is administered or ongoing therapy is modified (e.g, the dose of a pharmaceutical agent is increased or decreased) automatically. For example, the apparatus may interface with or include a device that modifies the infusion rate of a solution (optionally containing a therapeutic agent) in response to values for one or more of the hemodynamic variables measured according to the invention. By intermittently or continuously determining values for one or more hemodynamic variables and adjusting the infusion rate and/or dose of a therapeutic agent accordingly, the inventive system can operate using feedback, e.g., to provide closed-loop therapy. Specific desired values, or ranges of desired values, for the hemodynamic variables can be selected, e.g., by a patient's health care provider, and the apparatus can modify therapy in order to achieve these values. In certain embodiments of the invention the apparatus monitors and optionally records, stores, and/or analyzes the response of one or more of the hemodynamic variables to changes in therapy. The analysis can be used to make further adjustments or modifications to the therapeutic regimen. For example, the system can learn how particular therapies or alterations in therapy affect one or more hemodynamic variables and can select future therapy accordingly. In certain embodiments of the invention, suggested or recommended therapies or modifications to ongoing therapies are displayed on a display device.

A system or apparatus of the present invention may also include means for acquiring a circulatory signal from a subject. For example, a system or apparatus of the invention may include a catheter, e.g., a pulmonary artery catheter. If desired, certain of the signal processing steps may be performed by the acquisition means itself. For example, the acquisition means may include hardware for performing filtering, analog-to-digital conversion, analysis, etc., of the acquired signal.

The foregoing description is to be understood as being representative only and is not intended to be limiting. Alternative systems and techniques for implementing the methods of the invention will be apparent to one of skill in the art and are intended to be included within the accompanying claims. It will be appreciated that wherever the claims recite a method for determining one or more hemodynamic variables, the invention comprises apparatus and computer-executable process steps for performing the steps of the method and also comprises a method for monitoring a subject using the method for determining one or more hemodynamic variables and further comprises a method of treating a subject comprising monitoring a subject using the method and recommending, suggesting, selecting, modifying, and/or administering a therapy based at least in part on data and/or information acquired or obtained using the method, e.g., based at least in part on the subject's average LAP, average SVP, proportional CO, proportional PVR, and/or proportional SVR as determined according to the method. In addition, the methods and/or apparatus of the invention may be used to determine or monitor any one or more of these hemodynamic variables, e.g., any subset of these hemodynamic variables. All references cited herein are incorporated by reference. In the event of a conflict or inconsistency between any of the incorporated references and the instant specification, the specification shall control, it being understood that the determination of whether a conflict or inconsistency exists is within the discretion of the inventors and can be made at any time.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims, articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given method, apparatus, etc. unless indicated to the contrary or otherwise evident from the context. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim. In addition, it is to be understood that any one or more specific embodiments of the present invention may be explicitly excluded from the claims.

REFERENCES

1. Adamson, P B, A Magalski, F Braunschweig, M Bohm, D Reynolds, D Steinhaus, A Luby, C Linde, L Ryden, B Cremers, T Takle, T Bennett. Ongoing right ventricular hemodynamics in heart failure. clinical value of measurements derived from an implantable monitoring system. *J. Am. Coll. Cardiol.*, 41(4):565-571, 2003.

2. Alegret, J M, X Borras, F Carreras, I Duran, G Pons-Llado. Restrictive left ventricular filling and preserved ventricular function: a limitation in the noninvasive estimation of pulmonary wedge pressure by doppler echocardiography. *J. Am. Soc. Echocardiogr.*, 15(4):334-338, 2002.

3. Antonutto, G, M Girardis, D Tuniz, E Petri, C Capelli. Assessment of cardiac output from noninvasive determination of arterial pressure profile in subjects at rest. *Eur. J. Appl. Physiol.*, 69:183-188, 1994.

4. Bazett, H C. An analysis of the time-relations in electrocardiograms. *Heart*, 7:353-370, 1920.

5. Bourgeois, M J, B K Gilbert, D E Donald, E H Wood. Characteristics of aortic diastolic pressure decay with application to the continuous monitoring of changes in peripheral resistance. *Circ. Res.*, 35:56-66, 1974.

6. Bourgeois, M J, B K Gilbert, G von Bernuth, E H Wood. Continuous determination of beat-to-beat stroke volume from aortic pressure pulses in the dog. *Circ. Res.*, 39(1):15-24, 1976.

7. Burrus, C S, T W Parks. Time domain design of recursive digital filters. IEEE Trans. Audio Electroacoustics, 18:137-141, 1970.

8. Cerutti, C, M P Gustin, P Molino, C Z Paultre. Beat-to-beat stroke volume estimation from aortic pressure waveform in conscious rats: Comparison of models. *Am. J. Physiol.*, 281:H1148-H1155, 2001.

9. Chakko, S, D Woska, H Martinez, E de Marchena, L Futterman, K M Kessler, R J Myerberg. Clinical, radiographic and hemodynamic correlations in the chronic congestive heart failure: conflicting results may lead to inappropriate care. *Am. J. Med.*, 90:353-359, 1991.

10. Cibulski, A A, P H Lehan, H K Hellems. Pressure methods for estimating right and left ventricular stroke volumes. *Am. J. Physiol.*, 225(6):1460-1466, 1973.

11. Critchley, L A H. Impedance cardiography. the impact of new technology. *Anaesthesia*, 53:677-684, 1998.

12. Critchley, L A H, J A J H Critchley. A meta-analysis of studies using bias and precision statistics to compare cardiac output measurement techniques. *J. Clin. Monit. Comput.*, 15:85-91, 1999.

13. Dalibon, N, T Guenoun, D Joumois, J Frappier, D Safran, M Fischler. The clinical relevance of systolic pressure variations in anesthetized nonhypotensive patients. *J. Cardiothorac. Vasc. Anesth.*, 17(2):188-192, 2003.

14. deBoisblanc, B P, A Pellett, R Johnson, M Champagne, E McClarty, G Dhillon, M Levitzky. Estimation of pulmonary artery occlusion pressure by an artificial neural network. *Crit. Care Med.*, 31(1):261-266, 2003.

15. DeLoskey, A F, W W Nichols, C R Conti, C J Pepine. Estimation of beat-to-beat stroke volume from the pulmonary arterial pressure contour in man. *Med. & Biol. Eng. & Comput.*, 16:707-714, 1978.

16. Diamond, G A, C Jacob. Noninvasive prediction of pulmonary-capillary wedge pressure. *N. Engl. J. Med.*, 328(19):1423-1424, 1993.

17. Ehlers, K C, K C Mylrea, C K Waterson, J M Calkins. Cardiac output measurements. a review of current techniques and research. *Ann. Biomed. Eng.*, 14(3):219-239, 1986.

18. Engelberg, J, A B DuBois. Mechanics of pulmonary circulation in isolated rabbit lungs. *Am. J. Physiol.*, 196(2):401-414, 1959.

19. Erlanger J, D R Hooker. An experimental study of blood-pressure and of pulse-pressure in man. *Bull. Johns Hopkins Hosp.*, 12:145-378, 1904.

20. Gerhardt, U M W, C Scholler, D Bocker, H Hohage. Non-invasive estimation of cardiac output in critical care patients. *J. Clin. Monit.*, 16:263-268, 2001.

21. Gonzalez-Vilchez, F, M Ares, J Ayuela, L Alonso. Combine use of pulsed and color M-mode doppler echocardiography for the estimation of pulmonary capillary wedge pressure: an empirical approach based on an analytical relation. J. Am. Coll. Cardiol., 34(2):515-523, 1999.

22. Gonzalez-Vilchez, F, J Ayuela, M Ares, N S Mata, A G Gonzalez, R M Duran. Comparison of doppler echocardiography, color m-mode doppler, doppler tissue imaging for the estimation of pulmonary capillary wedge pressure. *J. Am. Soc. Echocardiogr.*, 15(10 Pt 2):1245-1250, 2002.

23. Goor, D, R Mohr. Method and apparatus for measuring the systemic vascular resistance of a cardiovascular system. U.S. Pat. No. 4,429,701. Feb. 7, 1984.

24. Gratz, I, J Kraidin, A G Jacobi, N G deCastro, P Spagna, G E Larijani. Continuous noninvasive cardiac output as estimated from the pulse contour curve. *J. Clin. Monit.*, 8:20-27, 1992.

25. Guyton, A C, J E Hall. *Textbook of Medical Physiology*. W. B. Saunders Company, Philadelphia, Pa., 1996.

26. Hallock, P, J C Benson. Studies on the elastic properties of human isolated aorta. *Am. J. Physiol.*, 16:595-602, 1937.

27. Henriquez, A H, F V Schrijen, J Redondo, N Delorme. Local variations of pulmonary arterial wedge pressure and wedge angiograms in patients with chronic lung disease. *Chest*, 94(3):491-495, 1988.

28. Herbert, W H. Limitations of pulmonary artery end-diastolic pressure as the reflection left ventricular end-diastolic pressure. *N.Y. State J. Med.*, 72:229, 1972.

29. Houtman, S, B Oeseburg, M T Hopman. Non-invasive cardiac output assessment during moderate exercise: pulse contour compared with co2 rebreathing. *Clin. Physiol.*, 19:230-237, 1999.

30. http://www.physionet.org/physiobank/database/mimicdb/

31. Humphrey, C B, R W Virgilio, T L Folkerth, R G Fosburg. An analysis of direct and indirect measurements of left atrial pressure. *J. Thorac. Cardiovasc. Surg.*, 71(5):643-647, 1976.

32. Imholz, B P M, W Wieling, G A van Montfrans, and K H Wesseling. Fifteen years experience with finger arterial pressure monitoring: Assessment of the technology. *Cardiovasc. Res.*, 38:605-616, 1998.

33. Kane, P B, J Askanazi, J F Neville, Jr., R L Mon, E L Hanson, W R Webb. Artifacts in the measurement of pulmonary artery wedge pressure. *Crit. Care Med.*, 6(1):36-38, 1978.

34. Kearney, T J, M M Shabot. Pulmonary artery rupture associated with the Swan-Ganz catheter. *Chest*, 108:1349-1352, 1995.

35. Kenner, T. ABP and its measurement. *Basic Res. Cardiol.*, 83(2):107-121, 1988.

36. Klabunde, R E. *Cardiovascular Physiology Concepts*. Lippincott Williams & Wilkins, Philadelphia, Pa., 2004.

37. Komadina, K H, D A Schenk, P La Veau. Interobserver variability in the interpretation of pulmonary artery catheter pressure tracings. *Chest*, 100:1647-1654, 1991.

38. Leatherman, J W, R S Shapiro. Overestimation of pulmonary artery occlusion pressure in pulmonary hypertension due to partial occlusion. *Crit. Care Med.*, 31(1):93-97, 2003.

39. Levett, J M, R L Replogle. Thermodilution cardiac output: a critical analysis and review of the literature. *J. Surg. Res.*, 27:392-404, 1979.

40. Linton, D M, D Gilon. Advances in noninvasive cardiac output monitoring. *Ann. Card. Anaesth.,* 5:141-148, 2002.
41. Linton, N W F, R A F Linton. Estimation of changes in cardiac output from the ABP waveform in the upper limb. *Br. J. Anaesth.,* 86:486-496, 2001.
42. Liu, C, C C Webb. Pulmonary artery rupture: serious complication associated with pulmonary artery catheters. *Int. J. Trauma Nurs.,* 6:19-26, 2000.
43. Ljung, L. *System Identification. Theory for the User.* PTR Prentice Hall, Englewood Cliffs, N.J., 1987.
44. Mammana, R B, S Hiro, S Levitsky, P A Thomas, J Plachetka. Inaccuracy of pulmonary capillary wedge pressure when compared to left atrial pressure in the early postsurgical period. J. Thorac. Cardiovasc. Surg., 84(3): 420-425, 1982.
45. Marik, P E. The systolic blood pressure variation as an indicator of pulmonary capillary wedge pressure in ventilated patients. *Anaesth. Intensive Care,* 21(4):405-408, 1993.
46. Marik, P, S O Heard, J Varon. Interpretation of the pulmonary artery occlusion (wedge) pressure: physicians' knowledge versus the experts' knowledge. *Crit. Care Med.,* 26(10):1761-1763, 1998.
47. Marino, P L. *The ICU Book.* Lippincott Williams & Wilkins, Baltimore, Md., 1998.
48. Martin, J F, L B Volfson, V V Kirzon-Zolin, V G Schukin. Application of pattern recognition and image classification techniques to determine continuous cardiac output from the arterial pressure waveform. *IEEE Trans. Biomed. Eng.,* 41(10):913-920, 1994.
49. McIntyre, K, J Vita, C Lambrew, J Freeman, J Loscalzo. A noninvasive method of predicting pulmonary-capillary wedge pressure. *N. Engl. J. Med.,* 327:1715-1720, 1992.
50. Medin, D L, D T Brown, R Wesley, R E Cunnion, F P Ognibene. Validation of continuous thermodilution cardiac output in critically ill patients with analysis of systematic errors. *J. Crit. Care,* 13(4):184-189, 1998.
51. Milnor, W R, A D Jose, C J McGaff. Pulmonary vascular volume, resistance, and compliance in man. *Circulation,* 22:130-137, 1960.
52. Moody, G B, R G Mark. A database to support development and evaluation of intelligent intensive care monitoring. *Comput. Cardiol.,* 23:657-660, 1996.
53. Morris, A H, R H Chapman, R M Gardner. Frequency of technical problems encountered in the measurement of pulmonary artery wedge pressure. *Crit. Care Med.,* 12(3): 164-170, 1984.
54. Mukkamala, R, A T Reisner, H M Hojman, R G Mark, R J Cohen. Continuous cardiac output monitoring by peripheral blood pressure waveform analysis. *Comput. Cardiol.,* 30:281-284, 2003.
55. Noordergraaf, A. *Circulatory System Dynamics.* Academic Press, New York, N.Y., 1978.
56. Parks, T W, C S Burrus. Digital Filter Design. John Wiley & Sons, Inc., New York, N.Y., 1987.
57. Poelzl, G, M Gattermeier, H Dratzer, E Zeindlhofer, P Kuehn. Feasibility and accuracy of transthoracic Doppler echocardiographic estimation of pulmonary capillary wedge pressure applying different methods. Eur. J. Heart Fail., 3(5):553-560, 2001.
58. Rapaport, E, L Dexter. Pulmonary "capillary" pressure. In J V Warren, editor, *Methods in Medical Research.* Year Book Publishers, Chicago, Ill., 7:85-93, 1958.
59. Redling, J D, M Akay. Noninvasive cardiac output estimation: A preliminary study. *Biol. Cybern.,* 77:111-122, 1997.
60. Remington, J W, W F Hamilton. The construction of a theoretical cardiac ejection curve from the contour of the aortic pressure pulse. *Am. J. Physiol.,* 144:546-556, 1945.
61. Reynolds, D W, N Bartelt, R Taepke, T D Bennett. Measurement of pulmonary artery diastolic pressure from the right ventricle. *JACC,* 25(5):1176-1182, 1995.
62. Richards, D R, Y Gilliland, J A Bernal, F W Smart, D D Stapleton, H O Ventura, J Cheirif. Mitral inflow and pulmonary venous doppler measurements do not predict pulmonary capillary wedge pressure in heart transplant recipients. *Am. Heart J.,* 135(4):641-646, 1998.
63. Rosenfeld, B A, T Dorman, M J Breslow, P Pronovost, M Jenckes, N Zhang, G Anderson, H Rubin. Intensive care unit telemedicine: alternate paradigm for providing continuous intensivist care. *Crit. Care Med.,* 28(12):3925-3931, 2000.
64. Sandham, J D, R D Hull, R F Brant, L Knox, G F Pineo, C J Doig, D P Laporta, S Viner, L Passerini, H Devitt, A Kirby, M Jacka. A randomized, controlled trial of the use of pulmonary-artery catheters in high-risk surgical patients. *N. Engl. J. Med.,* 348(1):5-14, 2003.
65. Sharma, G V R K, P A Woods, C T Lambrew, C M Berg, D A Pietro, T P Rocco, F W Welt, P Sacchetti, K M McIntyre. Evaluation of a noninvasive system for determining left ventricular filling pressure. *Arch. Intern. Med.,* 162:2084-2088, 2002.
66. Starmer, C F, P A McHale, F R Cobb, J C Greenfield. Evaluation of several methods for computing stroke volume from central aortic pressure. *Circ. Res.,* 33:139-148, 1973.
67. Steinhaus, D M, R Lemery, D R Bresnahan, Jr., L Handlin, T Bennett, A Moore, D Cardinal, L Foley, R Levine. Initial experience with an implantable hemodynamic monitor. *Circulation,* 93(4):745-752, 1996.
68. Stetz, C W, R G Miller, G E Kelly, T A Raffin. Reliability of the thermodilution method in the determination of cardiac output in clinical practice. *Am. Rev. Respirat. Dis.,* 126:1001-1004, 2982.
69. Stevenson, L W, J K Perloff. The limited reliability of physical signs for estimating hemodynamics in chronic heart failure. *JAMA,* 261:884-888, 1989.
70. Swan, H J C, W Ganz, J Forrester, H Marcus, G Diamond, D Chonette. Catheterization of the heart in man with the use of a flow-directed balloon-tipped catheter. *N. Engl. J. Med.,* 283:447-451, 1970.
71. Tajimi, T, K Sunagawa, A Yamada, Y Nose, A Takeshita, Y Kikuchi, M Nakamura. Evaluation of pulse contour methods in calculating stroke volume from pulmonary artery pressure curve (comparison with aortic pressure curve). *Eur. Heart J.,* 4:502-511, 1983.
72. Verdouw, P D, J Beaune, J Roelandt, P G Hugenholtz. Stroke volume from central aortic pressure? a critical assessment of the various formulae as to their clinical value. *Basic Res. Cardiol.,* 70:377-389, 1975.
73. Welkowitz, W, Q Cui, Y Qi, J B Kostis. Noninvasive estimation of cardiac output. *IEEE Trans. Biomed. Eng.,* 38(11):1100-1105, 1991.
74. Wesseling, K H, J R C Jansen, J J Settels, J J Schreuder. Computation of aortic flow from pressure in humans using a nonlinear, three-element model. *Am. J. Physiol.,* 74(5): 2566-2573, 1993.
75. Xu, H, S Zhou, W Ma, B Yu. Prediction of pulmonary artery wedge pressure from arterial pressure or pulse oximetry plethysmographic waveform. *Chin. Med. J.,* 115(9): 1372-1375, 2002.

76. Yelderman, M, M D Quinn, R C McKnown, R C Eberhart, M L Dollar. Continuous thermodilution cardiac output measurement in sheep. *J. Thorac. Cardiovasc. Surg.,* 104 (2):315-320, 1992.
77. Zacharoulis, A A, C J Mills, I T Gabe, J P Shillingford. Estimation of stroke volume from the pulmonary artery pressure record. *Cardiovasc. Res.,* 8:506-516, 1974.
78. Zollner, C, A E Goetz, M Weis, K Morstedt, B. Pichler, P Lamm, E Kilger, M Haller. Continuous cardiac output measurements do not agree with conventional bolus thermodilution cardiac output determination. *Can. J. Anaesth.,* 48(11):1143-1147, 2001.
79. deBloisblanc, B P, et al., U.S. Pat. No. 6,113,548.

We claim:

1. A method for determining an average left atrial pressure (LAP) using a cardiac cycle waveform signal, the method comprising:
    converting, by an analog-to-digital converter of an apparatus, a cardiac cycle waveform signal of a patient into a digital cardiac signal, the digital cardiac signal comprising a plurality of digital cardiac signal values;
    selecting, from a buffer system of the apparatus, two or more digital cardiac signal values from a first interval of the digital cardiac signal;
    fitting, by a processing unit of the apparatus, a nonlinear function to match the two or more digital cardiac signal values within the first interval;
    extrapolating, by the processing unit, a plurality of values of the nonlinear function for a second interval of the nonlinear function, the second interval of the nonlinear function corresponding to an interval of the digital cardiac signal that is different from the first interval; and
    determining, by the apparatus, one or more average left atrial pressure (LAP) values based on a mean value of the plurality of values of the extrapolated nonlinear function over a portion of the second interval.

2. The method of claim 1, further comprising determining, by the apparatus, a proportional cardiac output (CO) based at least in part on subtracting the one or more average LAP values from one or more digital cardiac signal values.

3. The method of claim 2, wherein the mean value is further based on a predetermined time constant, the predetermined time constant related to a duration of time within the second interval.

4. The method of claim 1, further comprising determining, by the apparatus, a proportional cardiac output (CO) based on a computed mean value that is responsive to a result calculated by subtracting the one or more average LAP values from the plurality of values of the extrapolated nonlinear function.

5. The method of claim 4, further comprising determining, by the apparatus, the proportional CO based at least in part by dividing the computed mean value by a duration of the second interval.

6. The method of claim 1, wherein the cardiac cycle waveform is a pulmonary artery pressure (PAP) signal of the patient.

7. The method of claim 1, wherein the cardiac cycle waveform is a right ventricular pressure (RVP) signal of the patient.

8. The method of claim 1, wherein the cardiac cycle waveform is a systemic arterial pressure (SAP) signal of the patient.

9. The method of claim 1, wherein the nonlinear function further comprises an exponential component.

10. The method of claim 9, wherein the nonlinear function is a mono-exponential function.

11. A method for determining an average left atrial pressure (LAP) using a cardiac cycle waveform signal, the method comprising:
    receiving a cardiac cycle waveform signal, the cardiac cycle waveform signal representing a cardiac output of a patient;
    converting the cardiac cycle waveform signal into a digital cardiac signal, the digital cardiac signal comprising a plurality of digital cardiac signal values, each of the plurality of digital cardiac signal values corresponding to a portion of the digital cardiac signal;
    selecting two or more digital cardiac signal values from within a first interval of the digital cardiac signal;
    fitting a nonlinear function to match the two or more digital cardiac signal values within the first interval;
    extrapolating a plurality of values of the nonlinear function for a second interval of the nonlinear function, the second interval of the nonlinear function corresponding to an interval of the digital cardiac signal that is different from the first interval; and
    determining one or more average left atrial pressure (LAP) values based on a mean value of the plurality of values of the extrapolated nonlinear function over a portion of the second interval, the one or more average LAP values representing a cardiac output of the patient.

12. The method of claim 11, further comprising determining a proportional cardiac output (CO) based at least in part on subtracting the one or more average LAP values from one or more digital cardiac signal values.

13. The method of claim 12, wherein the mean value is further based on a predetermined time constant, the predetermined time constant related to a duration of time within the second interval.

14. The method of claim 11, further comprising determining a proportional cardiac output (CO) based on a computed mean value that is responsive to a result calculated by subtracting the one or more average LAP values from the plurality of values of the extrapolated nonlinear function.

15. The method of claim 14, further comprising determining the proportional CO based at least in part by dividing the computed mean value by a duration of the second interval.

16. The method of claim 11, wherein the cardiac cycle waveform is a pulmonary artery pressure (PAP) signal of the patient.

17. The method of claim 11, wherein the cardiac cycle waveform is a right ventricular pressure (RVP) signal of the patient.

18. The method of claim 11, wherein the cardiac cycle waveform is a systemic arterial pressure (SAP) signal of the patient.

19. The method of claim 11, wherein the nonlinear function further comprises an exponential component.

20. The method of claim 19, wherein the nonlinear function is a mono-exponential function.

* * * * *

UNITED STATES PATENT AND TRADEMARK OFFICE
CERTIFICATE OF CORRECTION

PATENT NO. : 7,666,144 B2  Page 1 of 1
APPLICATION NO. : 11/358379
DATED : February 23, 2010
INVENTOR(S) : Cohen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this

Twenty-eighth Day of December, 2010

David J. Kappos
*Director of the United States Patent and Trademark Office*